United States Patent [19]

Rebre et al.

[11] Patent Number: 5,408,006

[45] Date of Patent: * Apr. 18, 1995

[54] SUPERABSORBENT ACRYLIC POWDERS PREPARED VIA IMPROVED SUSPENSION POLYMERIZATION

[75] Inventors: Shu R. Rebre, Vincennes; Christian Collette, Paris; Thierry Guerin, Fontenay S/Bois, all of France

[73] Assignee: Elf Atochem S.A., Puteaux, France

[*] Notice: The portion of the term of this patent subsequent to Mar. 14, 2012 has been disclaimed.

[21] Appl. No.: 104,756

[22] Filed: Aug. 12, 1993

[30] Foreign Application Priority Data

Aug. 12, 1992 [FR] France ................................ 92 09959

[51] Int. Cl.$^6$ ............................................. G08F 265/02
[52] U.S. Cl. ..................................... 525/301; 525/258; 525/273; 525/274
[58] Field of Search ............................................ 525/301

[56] References Cited

U.S. PATENT DOCUMENTS 4,745,154  5/1988  Ruffner .
4,783,510 11/1988  Saotome ........................ 525/329.7

FOREIGN PATENT DOCUMENTS 0441507  8/1991  European Pat. Off. .

*Primary Examiner*—Vasu S. Jagannathan
*Attorney, Agent, or Firm*—Burns, Doane, Swecker & Mathis

[57] ABSTRACT

Particulates of a superabsorbent polymer, e.g., an acrylic polymer such as polyacrylic acid, well suited for a variety of hygienic applications, are prepared by (i) suspending an aqueous solution of a water-soluble monomer charge I in a hydrocarbon medium by means of a polymerizable surfactant having the general formula:

$$R_1-O-(CH_2-CH_2-O)_n-R_2$$

wherein $R_1$ is a hydrocarbon having at least 9 carbon atoms, $R_2$ is an acryloyl, methacryloyl or maleoyl radical, and the degree of condensation n in respect of the ethylene oxide ranges from 30 to 70, (ii) polymerizing the suspension thus formed, producing a suspension of polymer gel particles and converting the surfactant to effectively remove same from the medium of polymerization, (iii) next absorbing a second monomer charge II into such gel particles, and (iv) polymerizing in the gel particles the second monomer charge II.

6 Claims, No Drawings

SUPERABSORBENT ACRYLIC POWDERS PREPARED VIA IMPROVED SUSPENSION POLYMERIZATION

BACKGROUND OF THE INVENTION

CROSS-REFERENCE TO COMPANION APPLICATIONS

Our copending applications Ser. Nos. 08/104,757 now U.S. Pat. No. 5,373,066 [Attorney Docket No. 006050-318] and 08/104,761 [Attorney Docket No. 006050-319], both filed concurrently herewith and incorporated by reference herein, and assigned to the assignee hereof.

BACKGROUND OF THE INVENTION

1. Field of the Invention

The present invention relates to the production of superabsorbent acrylic polymer powders capable of absorbing large amounts of water or aqueous fluids and are well suited for a variety of hygienic applications.

2. Description of the Prior Art

It is known to this art to produce polymer particulates having a high capacity for water absorption by inverse suspension polymerization of ethylenically unsaturated monomers, more particularly of acrylic monomers. The powders which are thus obtained swell greatly in the presence of water, providing gels of high mechanical strength. These properties are useful, inter alia, for the manufacture of sanitary appliances, e.g., sanitary napkins, for absorption and retention of body fluids.

One significant improvement in the production of such absorbent powders is described in EP-0,441,507, comprising polymerization of the acrylic monomer in at least two discrete stages. In a first discrete stage, an inverse suspension polymerization is carried out in conventional manner, such polymerization resulting in the formation of a gel. In a second stage, a fresh monomer charge is absorbed into this gel and polymerization thereof is initiated within the actual gel formed previously. If appropriate, this absorption/polymerization sequence can be repeated. In this fashion, polymeric resins are prepared having a particle size which is appreciably larger than the resins obtained via single inverse suspension polymerization. Their degree or extent of swelling in the presence of water, elastic modulus, plasticity and resistance to collapse under pressure of the gel, are also appreciably improved.

However, to attain this result, it is necessary to ensure that the second charge of monomer does indeed polymerize within the gel initially formed and does not itself separately polymerize in the form of an inverse suspension in the hydrocarbon phase. It is thus required to prevent the surfactant, which is always present in the reactor after the first polymerization stage, from dispersing the second charge of monomer. This is the reason it is necessary to cool the reaction mass resulting from the first polymerization before introducing the second charge of monomer. Such cooling stage, which is an essential characteristic of the process, is also extremely restrictive on an industrial scale because it considerably prolongs the manufacturing time and adversely affects the economics of the process.

SUMMARY OF THE INVENTION

Accordingly, a major object of the present invention is the provision of an improved process for the preparation of superabsorbent acrylic powders via two-stage radical suspension polymerization and wherein the absorption of the second acrylic monomer charge into the initial gel particles can be carried out at a temperature equal to or greater than 45° C.

Briefly, the present invention features suspending the first acrylic monomer charge in appropriate medium therefor by means of particular surfactants also polymerizable via radical polymerization, whereby such surfactants are effectively removed from the system to no longer serve as suspending agents for any original polymerization process.

DETAILED DESCRIPTION OF PREFERRED EMBODIMENTS OF THE INVENTION

More particularly according to the present invention, as the selection of suitable surfactants is extremely delicate in the first polymerization stage, the preferred polymerizable surfactants are compounds having the general formula:

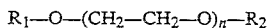

wherein $R_1$ is a hydrocarbon having at least 9 carbon atoms, $R_2$ is an acryloyl, methacrylol or maleoyl radical, and the degree of condensation n of the ethylene oxide ranges from 30 to 70.

Particularly preferred polymerizable surfactants include the maleic acid monoester of nonylphenol oxyethylenated with 50 molecules of ethylene oxide, the acrylic acid monoester of nonylphenol oxyethylenated with 45 molecules of ethylene oxide, and the methacrylic acid monoester of nonylphenol oxyethylenated with 50 molecules of ethylene oxide.

In general, the two-stage inverse suspension polymerization according to the invention proceeds in the following sequences, more fully described in the examples below:

(a) preparation of the hydrocarbon solvent phase;
(b) preparation of the aqueous monomer phase (charge I);
(c) suspending the monomer charge I in the hydrocarbon phase and conducting the polymerization I;
(d) preparation of the aqueous monomer phase (charge II),
(e) absorption of the charge II into the gel particles and conducting the polymerization II;
(f) isolation of the final polymer.

The process of the present invention thus features the preparation of polymers of water-soluble ethylenically unsaturated monomers such as acrylic acid, methacrylic acid and the nonionic derivatives thereof, such as acrylamide, methacrylamide and the N,N-dimethyl-substituted derivatives thereof; 2-hydroxyethyl acrylate or 2-hydroxyethyl methacrylate; N-methylol-acrylamide or N-methylol-methacrylamide, or the nitrogen-containing derivatives thereof, such as (dimethyl or diethyl-)amino(ethyl or propyl)acrylate or methacrylate and the corresponding quaternary ammonium salts thereof. Acrylic acid is the preferred ethylenically unsaturated monomer.

The polymerization is initiated by radical polymerization initiators, which are preferably water-soluble because both the monomer and the polymer are themselves hydrophilic. Potassium persulfate is particularly suitable according to the present invention. The various auxiliaries, additives and adjuvants used to prepare hydrophilic polymers by suspension polymerization are also well known to this art, and include the protective colloids which physically accompany the emulsifiers as an accessory for physically stabilizing the reactants converted into suspension, for example modified celluloses, polyethylenes or their copolymers which have been oxidized or modified with maleic anhydride. These also include crosslinking agents for the partial crosslinking of the hydrophilic polymers produced, such crosslinking agents being compounds comprising at least two unsaturated groups which are copolymerizable with the unsaturated monomer (acrylic acid), typical examples being diacrylates and triacrylates of polyols, or capable of reacting with its polymerization products, such as the diglycidyl ethers of diols.

Exemplary solvents for establishing the inverse suspension include various aliphatic, cycloaliphatic or aromatic hydrocarbons, with the preferred solvent being heptane.

According to the invention, the polymerizable surfactant is introduced during the sequence (b), and since it disappears from the reaction medium at the end of sequence (c), it is not required to conduct more than modest cooling of the reactor, to a temperature equal to or greater than 45° C., such that sequence (e), namely, the absorption of the monomer, is carried out a temperature which is not excessive, but which, however, need not be below 35° C. Should the suspension appear to lack stability after the absorption sequence, this can be corrected, if necessary, by adding a dispersant to the composition, the nature of which not being critical. In particular, a complementary emulsifier can be used, such emulsifiers being known to this art, to the extent that the sequences (d) to (f) are not repeated.

Unexpectedly, the process of the invention permits a very substantial gain in productivity, the extent of which becomes apparent taking account of the fact that adjusting the absorption temperature of the second charge to from 18° C. to 35° C. entails substantial cooling of the reactor, whereas, after the first polymerization if it has to be cooled to only 45° C. an ostensibly negligible gain in time on a laboratory scale, the increase in productivity on an industrial scale is, in contrast, about 30%.

In order to further illustrate the present invention and the advantage thereof, the following specific examples are given, it being understood that same are intended only as illustrative and in nowise limitative.

EXAMPLE 1

Sequence (a)

Into a one liter reactor equipped with means for introducing solid or liquid reactants, a stirrer, a system for flushing with neutral gas, a temperature probe and heating and cooling means, there were introduced 265.6 g of heptane which were heated to 80° C., and in which there was dissolved, with stirring at 400 rpm, 0.92 g of a polyethylene modified with maleic anhydride, this being a product marketed by Mitsui Petrochemical Industries under the trademark HI-Wax 1105A and which served as a protective colloid.

Sequence (b)

Separately, 92 g of an 80% by weight aqueous solution of acrylic acid were neutralized with 139.4 g of 22% strength sodium hydroxide solution. Then, 0.276 g of hydroxyethylcellulose was added, followed by 5.5 g of a 1% strength aqueous solution of potassium persulfate, 0.92 g of a 2% strength aqueous solution of ethylene glycol diglycidyl ether and 0.46 g of maleic acid ester of nonylphenol containing 50 moles of ethylene oxide (Aerosol MEM-NP 50 marketed by Cyanamid). It will be appreciated that this emulsifier was introduced into the aqueous charge, which is rather unusual when it is desired to form an inverse suspension.

Sequence (c)

While continuing to stir the reactor at 400 rpm and flushing it with nitrogen at the rate of 80 liters/minute, the previously prepared aqueous phase was introduced, small amounts at a time, and was converted into inverse suspension in the heptane. The temperature was increased to 70° C. to initiate the polymerization; it was maintained at this level for 30 minutes. The temperature was then decreased to 45° C.

Sequence (d)

While the preceding operation was being carried out, 92 g of an 80% by weight aqueous solution of acrylic acid were separately neutralized with 139.4 g of a 20% sodium hydroxide solution, after which 5.5 g of a 1% strength aqueous potassium persulfate solution and 0.92 g of a 2% strength aqueous ethylene glycol diglycidyl ether solution were added. This aqueous phase, which constituted the monomer charge II, was then adjusted to 10° C.

Sequence (e)

The stirring in the reactor was increased to 800 rpm while continuing the flushing with nitrogen at 80 liters/minute. The charge II was introduced small amounts at a time. After the charge II had been introduced, the absorption was allowed to continue for 5 minutes at a temperature of about 35° C. Thereafter, the temperature was increased to 70° C. to initiate the second polymerization phase. The polymerization was permitted to proceed for 30 minutes.

Final sequence (f)

The heptane and the greater fraction of the water were removed by distillation. Then, 1.84 g of a 2% strength aqueous solution of ethylene glycol diglycidyl ether were added to the contents of the reactor and the product was dried under nitrogen.

A powder having a mean particle size of 370 μm, none of which passed through a 100 μm screen, was thus obtained. The results were not significantly different when the absorption sequence was carried out at 50° C.

EXAMPLE 2 (Comparative)

The operations of Example 1 were repeated except that in sequence (b), instead of 0.46 g of Aerosol MEM-NP 50, 0.46 g of the acrylic acid monoester of nonylphenol oxyethylenated with 20 molecules of ethylene oxide was introduced as the emulsifier.

The polymerization proceeded very differently in sequence (c): the contents of the reactor set solid and it was impossible to continue the process.

EXAMPLE 3 (Comparative)

This example was carried out using an emulsifier according to the prior art, which functioned correctly if the absorption sequence was carried out strictly at a low temperature (20° C.). An attempt to reproduce the operation at an absorption temperature of 35° C. was unsuccessful.

Sequence (a)

Into the apparatus described in Example 1, 265.6 g of heptane were introduced and heated to 80° C. and 0.74 g of sucrose disteatate/tristearate and 0.92 g of polyethylene modified with maleic anhydride were dissolved therein, with stirring at 400 rpm.

Sequence (b)

Separately, 92 g of an 80% by weight aqueous solution of acrylic acid were neutralized with 139.4 g of a 22% strength sodium hydroxide solution. Then, 0.276 g of hydroxyethylcellulose was added, followed by 5.5 g of a 1% strength aqueous solution of potassium persulfate and 0.92 g of a 2% strength aqueous solution of ethylene glycol diglycidyl ether.

The downstream sequences (c) and (d) were carried out as in Example 1. The final product was a powder whose mean particle size was 150 μm, and of which the amount passing through a 100 μm screen was unacceptable, having a value greater than 15%.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of particulates of a superabsorbent polymer, comprising (i) suspending an aqueous solution of a water-soluble monomer charge I in a hydrocarbon medium by means of a polymerizable surfactant having the general formula:

$$R_1-O-(CH_2-CH_2-O)_n-R_2$$

wherein $R_1$ is a hydrocarbon having at least 9 carbon atoms, $R_2$ is an acryloyl, methacryloyl or maleoyl radical, and the degree of condensation n in respect of the ethylene oxide ranges from 30 to 70, (ii) polymerizing the suspension thus formed, producing a suspension of polymer gel particles and converting said surfactant to effectively remove same from the medium of polymerization, (iii) next absorbing a second monomer charge II into said gel particles, and (iv) polymerizing in the gel particles said second monomer charge II, wherein said (iii) absorbing the second monomer charge II into said gel particles is carried out at a temperature of at least about 45° C.

2. The process as defined by claim 1, comprising isolating the superabsorbent polymer particulates thus obtained.

3. The process as defined by claim 1, said monomer charges I and II comprising an acrylic monomer.

4. The process as defined by claim 3, said acrylic monomer comprising acrylic acid.

5. The process as defined by claim 1, said hydrocarbon medium comprising heptane.

6. The process as defined by claim 1, said polymerizable surfactant comprising the maleic acid monoester of nonylphenol oxyethylenated with about 50 molecules of ethylene oxide, the acrylic acid monoester of nonylphenol oxyethylenated with about 45 molecules of ethylene oxide, or the methacrylic acid monoester of nonylphenol oxyethylenated with about 50 molecules of ethylene oxide.

* * * * *